United States Patent [19]
del Valle et al.

[11] Patent Number: 5,255,568
[45] Date of Patent: Oct. 26, 1993

[54] LIQUID SAMPLE/REAGENT METERING AND DELIVERY METHOD

[75] Inventors: Roberto del Valle, Miami; Santos E. Vargas, Hialeah; Pedro P. Cabrera, Miami, all of Fla.

[73] Assignee: Coulter Corporation, Miami, Fla.

[21] Appl. No.: 965,095

[22] Filed: Oct. 22, 1992

Related U.S. Application Data

[63] Continuation of Ser. No. 626,936, Dec. 13, 1992, Pat. No. 5,158,751.

[51] Int. Cl.$^5$ .............................. G01N 1/10; G01N 1/20
[52] U.S. Cl. .................................. 73/863.73; 422/103; 436/180; 251/355
[58] Field of Search ...................... 422/103; 73/863.73, 73/864.12; 251/355; 436/180, 17, 45

[56] References Cited

U.S. PATENT DOCUMENTS

| | | | |
|---|---|---|---|
| 4,445,391 | 5/1984 | Cabrera | 73/864.12 |
| 4,507,977 | 4/1985 | Cabrera | 73/864.12 |
| 4,702,889 | 10/1987 | Cabrera et al. | 422/103 |
| 4,822,569 | 4/1989 | Pellegrino | 422/103 |
| 4,896,546 | 1/1990 | Cabrera et al. | 73/863.73 |
| 4,948,565 | 8/1990 | Bemis et al. | 422/103 |
| 4,957,008 | 9/1990 | Proni et al. | 73/864.83 |
| 5,158,751 | 10/1992 | del Valle et al. | 422/103 |

Primary Examiner—James C. Housel
Assistant Examiner—N. Bhat
Attorney, Agent, or Firm—Sidney N. Fox

[57] ABSTRACT

A method for sampling, metering and delivering precise microliter volume aliquots of a liquid blood sample to mixing and testing means of an electronic blood analysis system for analysis using a sampling and metering valve assembly in which is defined plural through fluid flow paths, one of the flow paths including a loop for metering and isolating a sample aliquot therein, the method comprising the steps of defining first and second dedicated passages within the valve assembly displaced one from the other and from the loop containing the isolated aliquot, introducing an inert gas to the loop to force the aliquot therein to said first dedicated passage at the displaced location thereof, placing the first and second dedicated passages in communicating relationship and introducing lyse reagent to the second dedicated passage to force the isolated aliquot from the first dedicated passage with the lyse reagent to a location exterior of the valve assembly without contaminating any flow paths which has been traversed by the liquid sample or a fluid other than the lyse reagent.

12 Claims, 5 Drawing Sheets

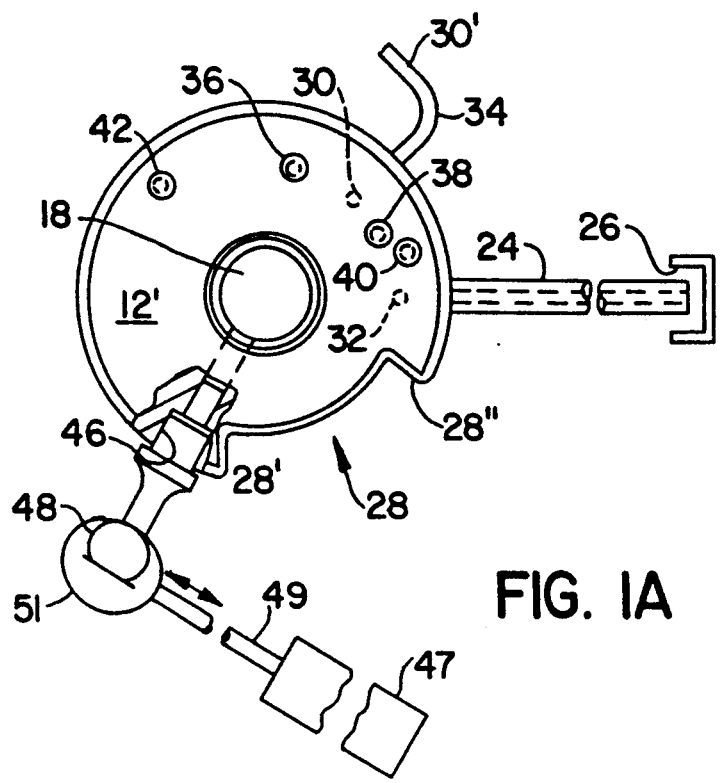
FIG. IA
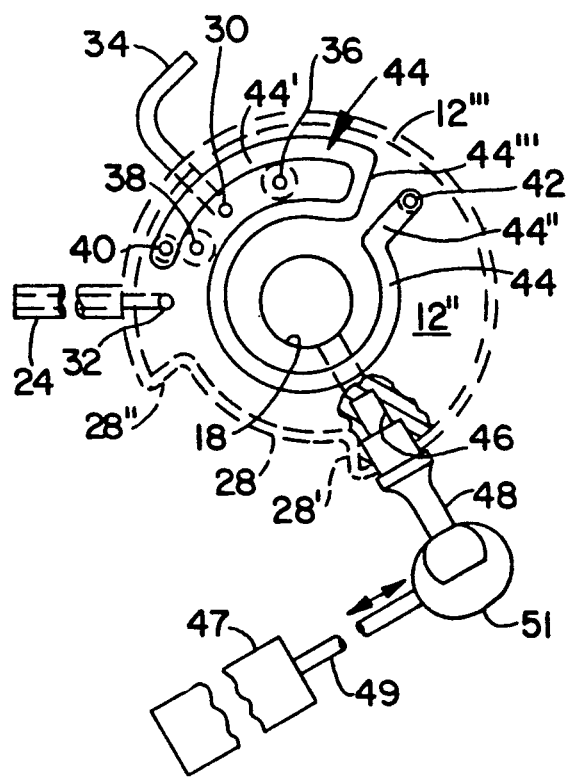
FIG. IB
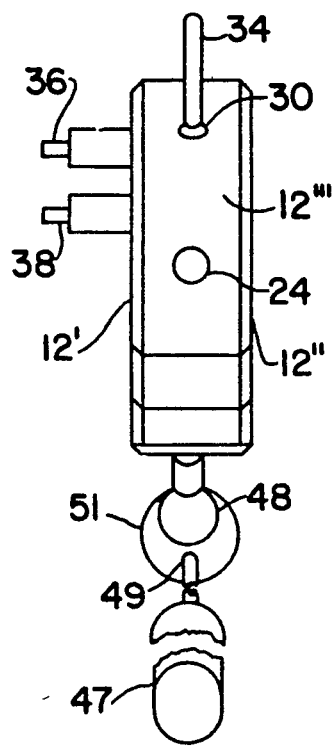
FIG. IC

LIQUID SAMPLE/REAGENT METERING AND DELIVERY METHOD

REFERENCE TO RELATED APPLICATION

This application is a continuation of our copending application Ser. No. 07/626,936 filed Dec. 13, 1992 entitled "A LIQUID METERING AND TRANSFER VALVE ASSEMBLY" now allowed U.S. Pat. No. 5,158,751.

CROSS-REFERENCE TO RELATED PATENTS

The following patents are incorporated by reference in the instant application for the disclosures thereof:

| | | |
|---|---|---|
| 2,656,508 | Coulter et al | October/1953 |
| 3,549,994 | Rothermel et al | December/1970 |
| 3,567,390 | Rothermel | March/1970 |
| 4,152,391 | Cabrera | May/1979 |
| 4,445,391 | Cabrera | May/1984 |
| 4,507,977 | Cabrera | Apr/1985 |
| 4,702,889 | Cabrera et al | October/1987 |
| 4,896,456 | Cabrera et al | January/1990 |

FIELD OF THE INVENTION

This invention relates generally to methods for using sampling valve assemblies for sampling, metering, isolating, transferring and delivering precise microliter volume aliquots of a whole blood sample from a single source thereof, to mixing and testing means of a blood analysis system located exterior of the valve assembly.

More particularly, the invention provides a method for sampling and metering a liquid blood sample using such a valve assembly of the character described, isolating an aliquot of said sample within said valve assembly and delivering said sample from the valve assembly using a reactive reagent, such as lyse, as the driving force, the said reagent being introduced into the valve assembly to effect said delivery without contaminating any interior passages within the valve assembly which had been traversed by the blood sample or any fluid other than said reagent.

The method of the invention employs the valve assembly disclosed and claimed in our co-pending application Ser. No. 07/626,936 and enables the introduction of a reagent, such as a lysing reagent, into the sampling valve assembly which contains an isolated precise volume sample aliquot, as the driving force for delivering the aliquot, with the lysing reagent, from the valve assembly to an exterior located predetermined location, such as the mixing and/or testing means of the blood analysis system and without contaminating any interior flow paths within the valve assembly which may have been traversed by the blood sample or a fluid other than the lysing reagent.

Reference has been made to U.S. Pat. Nos. 2,656,508, 3,549,994 and others. The valve assemblies to which reference has been made preferably comprise a pair of stationary valve disc elements sandwiching a center, rotatable valve disc element, said elements arranged coaxially with the faces of the center element frictionally sealingly engaged with the adjacent faces of the stationary elements. These valve assemblies have achieved considerable commercial success and have included internal passageway means of precise interior volume to provide precise volumes of liquid sample for dilution. Preferably, a series flow path was defined through the valve assembly for the receipt of a continuous body of blood sample from a source thereof. This series flow path included segmenting passageway means and segmenting portions, each have a precise interior volume. Upon rotation of the center valve element, the loaded series flow path was segmented to define the precise volume aliquot portions which were individually isolated. Predetermined volumes of diluent were introduced to each of the aliquot portions driving respective ones with associated diluent to mixing and testing vessels exterior of the valve assembly for the determination of various parameters of the blood sample. The determination of certain of said parameters requires the lysing of the dilution with lysing reagent. It would also be advantageous to measure the aliquot of blood sample which is to be lysed simultaneously with the measurement of the other blood sample aliquots so that all would constitute the same batch and would thus be better correlated. Further, it would be most advantageous to effect the drawing of all three sample portions in a single step. This would be most efficiently effected by employing a single metering and transfer valve. Heretofore this has not be possible since the lysing reagent has corrosive properties and, of course, would contaminate those interior portions of the valve assembly which carry the blood samples or which may contact either the diluent or blood flow paths within the valve assembly, and hence contaminate those samples and/or dilutions which must not be exposed to the lysing reagent. Even traces of lysing reagent would deleteriously effect the other liquids traversing the interior of the valve assembly.

Accordingly, the exposure of the valve assembly interior to or the presence of any lysing reagent within the valve assembly used to provide dilutions has to be avoided. Thus, addition of such reagent conventionally occurs outside the valve assembly along individual dedicated lines and flow paths leading from a source of lysing reagent to the specific mixing and testing vessel containing the blood sample dilution which must be treated therewith. This has required a separate valve assembly additional to the blood metering and transfer valve.

It has become desirous to determine certain characteristics of whole blood by means other than apparatus based directly upon the Coulter principle yet provide for such determinations via the same instrument operating under the Coulter principle. This may require lysing of an undiluted whole blood sample with lysing reagent. To accomplish such task, a second or additional blood sampling and transfer valve assembly was required to be dedicated to the task of metering a blood sample aliquot and, either directly or indirectly handling the lysing reagent through that valve assembly or to direct the measured blood sample undiluted to a location where lysing reagent can be mixed therewith. With a separate blood sampling and transfer valve, all the blood characteristics determined would not arise from the same sample. If the lyse reagent was handled within the valve assembly, a residual trace or greater of lysing reagent remained therewithin and great care and effort was required to remove such trace by multiple rinsing with detergents and diluent. If one attempted to direct lysing reagent through the same valve assembly used to provide the dilutions as used to provide the non-diluted volume for lysing, the poisoning of the interior flow paths with lysing reagent was unavoidable under the available valve assembly constructions. Further, conservation of the available blood sample is a problem because such sample quantities were limited. As implied above, it also is important that all the determinations of the blood characteristics of a sample be determined from a sample taken from the same source batch, preferably at the same time.

SUMMARY OF THE INVENTION

The invention provides a method of introducing a reactive reagent, such as a lysing reagent, to one of an isolated whole blood aliquot within a sampling valve assembly and comprising the steps of defining first and second dedicated passages within the valve assembly displaced one from the other and from the isolated aliquot, introducing a first fluid from a source thereof to the isolated aliquot to force the aliquot to the first dedicated passage at the displaced location thereof, placing the first and second dedicated passages in communicating relationship, and introducing a second fluid, the reactive reagent, to the second dedicated passage to force the isolated aliquot with reactive reagent from the first dedicated passage to an exterior location without contaminating any interior passage within the valve assembly which has been traversed by the sample or a fluid other than the second fluid.

BRIEF DESCRIPTION OF THE DRAWINGS

FIGS. 1A and 1B are plan views of the outer rotor element of the valve assembly according to the invention;

FIG. 1C is a fragmentary top view of the outer rotor element illustrated in FIGS. 1A and 1B;

DESCRIPTION OF PREFERRED EMBODIMENTS

Figure 2A:
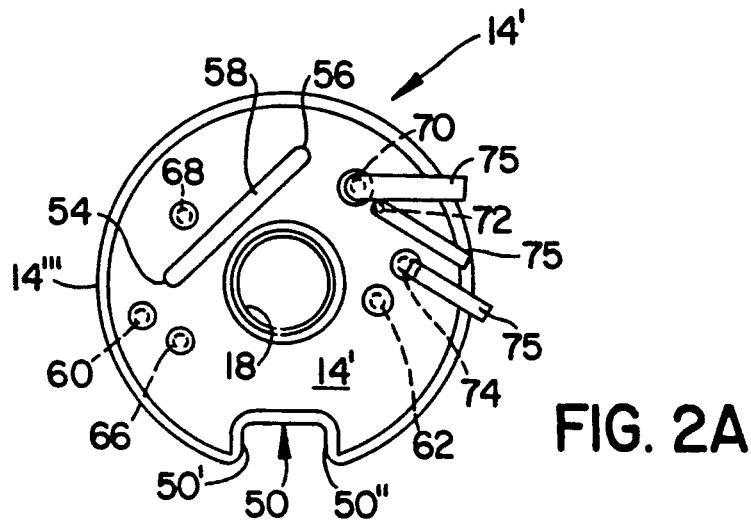
FIGS. 2A and 2B are plan views of the stator element of the valve assembly according to the invention.

The referenced patents provided a rotary three-disc whole blood metering and transfer valve assembly capable of metering blood sample aliquot volumes or portions and combining each of the sample aliquots with predetermined volumes of diluent for forming and delivering precise dilutions of said sample aliquots to exterior mixing and testing chambers. In addition to the dilutions, the invention provides means for metering and isolating an additional (selected) sample aliquot volume from the same sample source simultaneously with the other sample aliquots and delivering said selected sample aliquot volume with a volume of lysing reagent to an additional mixing and testing chamber, say for determination of a 5-part differential analysis of the said blood sample. Fluid, such as air or other inert gaseous fluid, is employed to position the selected aliquot sample volume at a location displaced from the rotor element of the valve assembly and the lysing reagent being passed through the valve assembly along a dedicated path therefor therewithin flushing both said sample aliquot and lysing reagent to said additional mixing and testing chamber whereby the flow paths within said valve assembly traversed by the whole blood sample and the diluent associated therewith are maintained free of contamination by the lysing reagent.

Referring to the drawings, the valve assembly according to the invention is designated generally in the FIGURES by reference character 10 and comprises an outer rotatable element hereinafter referred to as the loading element 12 (illustrated in FIGS. 1A through 1C), an outer stationary element, hereinafter referred to as the stator 14 (illustrated in FIGS. 2A through 2C and the center, rotatable element, hereinafter referred to as the rotor 16 (illustrated in FIGS. 3A through 3C). The loading element 12, the stator 14 and the rotor 16 each have an axial mounting passage 18 and are mounted coaxially on a spindle 20 with their facing surfaces frictionally sealingly engaged. The said elements having the same diameter with the outer elements 12 and 14 being of the same thickness and the center element 16 being thinner than elements 12 and 14.

The loading element 12 is translatable between two angular positions, the first being adapted to enable reception of the whole blood sample via piercing needle means 22 such as described in U.S. Pat. No. 4,387,076 in a mode described as an automatic aspiration mode. The loading element is adapted, when placed in the second angular position, to enable reception of the whole blood sample via aspirator probe 24 secured thereto, in what shall be termed a manual aspiration mode. The loading element 12 is provided with an arcuate circumferential notch 28 opening to the outer circumferential surface 12''' and having opposite walls 28' and 28'' functioning to define the rotational limits between the automatic and manual aspiration positions.

The loading element 12 is provided with a pair of spaced angular sample inlet passageways 30 and 32 opening at their outer ends to the circumferential surface 12''' of loading element 12 while opening at their inner ends to the inner facing surface 12''. Both angular passageways 30 and 32 have radial portions 30' and 32' and inner, axially parallel portions 30'' and 32'' which open to said surface 12''. Suitable elbow 34 is seated securely within the radial portion 30' to provide for coupling to the piercing needle means 22 and the aspiration probe 24 is seated securedly within the radial portion 32'. Through axially parallel passageways 36 and 38 are formed in the loading element 12 spaced the same center to center distances from the axially parallel portions 30'' and 32'' of said angular passageways 30 and 32 respectively, the center axes of said passageways 36 and 38 and the axially parallel portions 30'' and 32'' intersecting a circular line concentric with the axial passage 18. The loading element 12 also carries axially parallel passageways 40 and 42.

Axially parallel through passageways 36 and 38, which can be described as complementary cooperating counterpart passageways, cooperate with angular passageways 30 and 32 respectively to direct diluent to the whole blood sample aliquot volume subsequent to isolation thereof (when the valve assembly has been placed in the segmentation or isolation [delivery] mode). Axially parallel passageways 40 and 42 open to the catch channel means 44 formed in the inner surface 12" of the loading element and serve as the inlet and outlet respectively for rinse liquid functioning to flush the said catch channel means 44 of any material which may have accumulated therein after escaping from the junctions of any interior passageways, said junctions being located at the frictionally engaged surfaces of said loading element 12 and the rotor 16 and which may have travelled along said surfaces toward the inner and/or the outer circumference of said valve assembly 10, say by capillarity.

The loading element 12 also is provided with a radially directed socket 46 opening to the outer circumferential surface 12'''. A stud 48 is seated securely within said socket 46 and extends outward thereof terminating with a ball-like formation 48'. A fluid activated cylinder 47 can be provided exterior of the valve assembly 10 for reciprocably operating piston rod 49. The free end of piston rod 49 can be coupled to the member 51 which is provided with a recess 53 conforming to the formation 48'. Formation 48' is secured to member 51 and receives said formation 48'. Thus the operation of the piston rod 51 enables the loading element 12 to be selectively rotated mechanically to select either the automatic or the manual aspiration or loading modes, the angular rotation required to reach one or the other of said modes being 45 degrees.

The loading element 12 is illustrated in FIG. 1A viewing the outer surface 12' while in FIG. 1B, the loading element 12 is illustrated with the surface 12" facing the viewer. As shown in FIG. 1B, the first catch-channel means 44 is formed in the surface 12" of the said loading element 12 and comprises an outer, arcuate portion 44' into which passageway 40 opens, an inner generally circular portion 44" (which extends substantially surrounding the axial passage 18), a linking portion 44''' joining portions 44' and 44" and a radially directed portion 44" into which the passageway 42 opens.

Figure 2B:
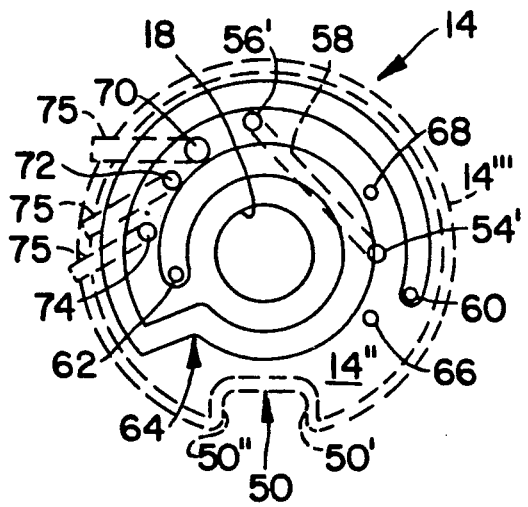
Figure 2C:
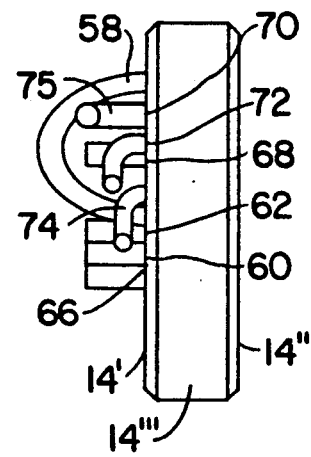
FIG. 2C is a side elevational view of the stator element illustrated in FIGS. 2A and 2B.

The stator element 14 of valve assembly 10 is illustrated in FIGS. 2A through 2C, the outer surface 14' facing the viewer in FIG. 2A and the inner surface 14" facing the viewer in FIG. 2B. The stator 14 is provided with a pair of opposite parallel surfaces, outer surface 14' and inner surface 14". Stator 14 also hs an outer circumferential surface 14''' and an axial passage 18 to receive the spindle 20. The stator 14 is provided with a rectangular configured circumferential notch 50 having opposite walls 50' and 50" and opening to the outer circumferential surface 14''', the notch 15 functioning so cooperate with means (not shown) to immobilize the stator 14 and prevent its angular movement.

Axially parallel through passageways 54 and 56 are formed in the stator 14. A first hollow loop 58 is seated sealingly securely within the openings 54' and 56' of passageways 54 and 56 to the surface 14' of said stator 14 so that the loop 58 extends outward of said outer surface 14'. The first hollow loop 58 has a precise interior volume suitable to define an aliquot volume of whole blood sample employed for the WBC determination as diluted with a predetermined volume of diluent.

The stator 14 carries axially parallel through passageways 60 and 62 formed therein. Second catch-channel means 64 are is formed in the inner surface 14" with the axially parallel passageways 60 and 62 opening thereinto, passageway 60 defining the entry for rinse liquid and passageway 62 defining the outlet for rinse liquid flushing the second catch-channel means 64 of any accumulated material which may have been intercepted within the second catch-channel means 64 after escaping from the junctions of any of the internal passageways at the facing surfaces 14" and 16" (of the rotor 16). The stator 14 also is provided with axially parallel through passageways 66, 68, 70, 72 and 74. Passageway 66 functions as the outlet for whole blood sample during the loading mode of the valve assembly 10 and functions as the inlet for feeding rinse liquid (backwash) to the flow path of said whole blood sample while the valve assembly 10 is in the returned or backwash mode. Passageway 68 functions as a dedicated passageway through which lysing reagent is passed during the delivery of said lysing reagent to flush a selected blood sample aliquot volume in accordance with the invention herein. The passageway 68 also functions as a portion of the flow path for the said selected whole blood sample as it is flushed from its isolated location within the valve assembly to a location displaced from said isolated location and free of the rotor by a fluid which may be a gaseous fluid such as air or an inert gas, in accordance with the invention herein, as will be described hereinafter.

Passageway 70 functions to introduce the inert fluid, such as air from an air pump, to the isolated location for the aforementioned selected whole blood sample aliquot volume for directing said aliquot volume from its isolated location to its displaced location via the dedicated passageway 68. Passsageway 72 serves two functions alternatively. During the loading mode, passageway 72 is coupled to a source of vacuum as to draw the sample into the probe 24. During the backwash or rinse mode, passageway 72 is coupled to a source of rinse liquid (diluent) in the form of a pump, to force said rinse liquid (diluent) along the path traversed by the WBC aliquot volume. Passageway 74 functions as an outlet to direct the whole blood sample aliquot volume isolated within the valve assembly 10, which aliquot volume is employed for the determination of the RBC characteristics of the whole blood sample, to the RBC mixing and testing chamber 52 by the introduction of a predetermined volume of diluent to flush same to said last mentioned isolated aliquot volume and form the required dilution. Suitable elbows 75 are seated in the respective passageways' openings to the outer surface 12' of the stator 14 to enable the couplings to be made for enabling the functions of said respective passageways to occur as described.

Figure 3C:
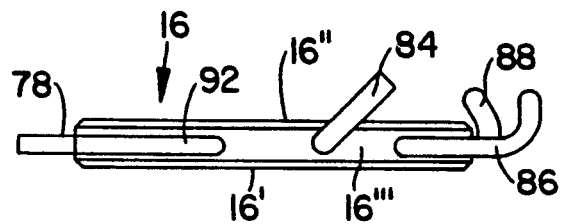
FIG. 3C is a top view of the rotor element illustrated in FIGS. 3A and 3B.
Figure 3A:
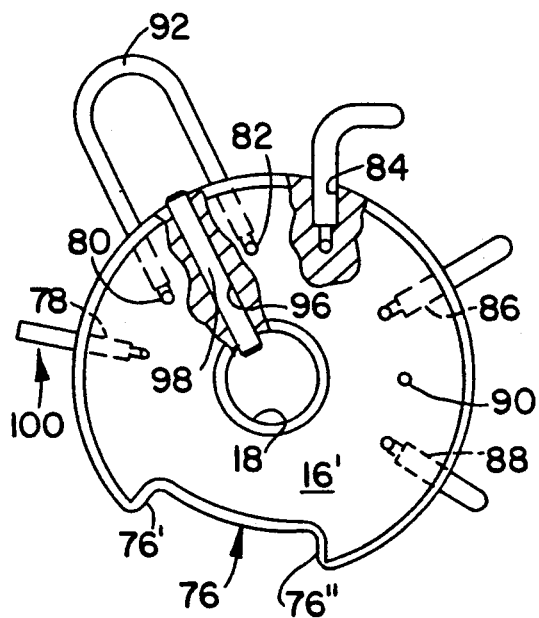
FIGS. 3A and 3B are plan views of the rotor element of the valve assembly according to the invention.
Figure 3B:
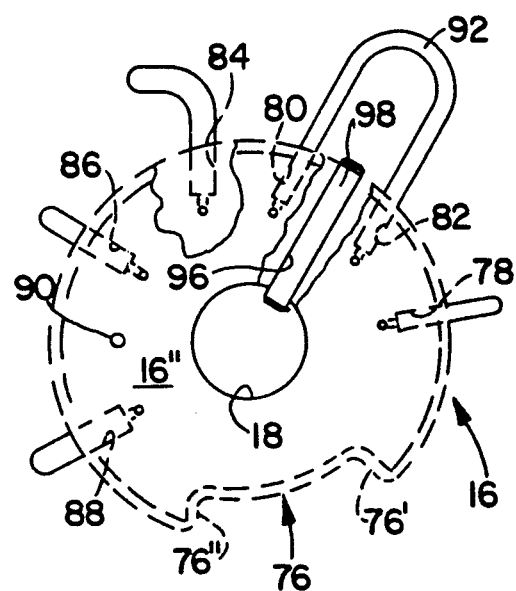

Attention now is directed to FIGS. 3A through 3C wherein the center rotatable elememt, rotor 16, of the valve assembly 10 is illustrated. Rotor 16 is provided with opposite parallel surfaces 16' and 16", along with outer circumferential surface 16" . In FIG. 3A, the rotor 16 is illustrated with its surface 16' facing the viewer, said surface being frictionally sealingly engaged with the surface 12" of the loading element 12 when the valve assembly 10 is assembled in operating condition. In FIG. 3B, the rotor 16 is illustrated with its surface 16" facing the viewer, said surface being frictionally sealingly engaged with the surface 14" of the stator 14 when the valve assembly 10 is assembled in operating condition. The rotor 16 has the same diameter as the loading element 12 and the stator 14 and is provided with a circumferential arcuate notch 76 opening to the outer circumferential surface 16''', said notch 76 having opposite walls 76' and 76" serving to limit the rotation of the rotor 16. As illustrated in FIGS. 3A and 3B, the rotor 16 is disposed in its orientation at the aspirating or loading mode of operation.

The rotor 16 is provided with six angular passageays 78, 80, 82, 84, 86 and 88, having their entry openings formed through the circumferential surface 16''' of said rotor 16 to enter their radially inward portions to intersect with their axially parallel portions respectively opening to the surface 16" of the rotor 16. Suitable elbows are seated within the radial portions of the respective angular passageways to permit communication with the exterior of the valve assembly 10. An axially parallel through passageway 90 is provided in rotor 16, said passageway 90 having a precise interior volume and functioning as the isolating or measuring chamber for the RBC whole blood sample aliquot volume which is isolated therein when the rotor 16 is translated to place the valve assembly 10 in the segmenting or isolating (delivery) mode of operation, as will be described hereinafter.

Passageway 78 functions as the inlet for introducing lysing reagent into the valve assembly 10 for the delivery of the aforementioned selected isolated whole blood sample aliquot, as will be described hereinafter. Passageways 80 and 82 seat the second hollow loop 92 sealing secured engaged within the radial portions thereof, said second loop 92 functioning as the measuring or isolating chamber for the selected whole blood aliquot which is to be treated with lysing reagent. Passageway 86 functions as the inlet for feeding the predetermined volume of diluent to the first hollow loop 58 for flushing the isolated content thereof to the WBC mixing and testing chamber 94 during the delivery of the WBC dilution to said chamber 94 when the valve assembly is placed in the segmentation and delivery mode of operation subsequent to the loading of the valve assembly with the whole blood sample. Passageway 84 functions to introduce rinse liquid (diluent) to the flow path of the RBC aliquot volume during the backwash of the flow path traversed by the RBC aliquot volume. Passageway 88 functions as the outlet for directing the WBC aliquot volume from the first hollow loop 58 to the WBC mixing and testing chamber 94 along with the predetermined volume of diluent introduced to the first loop 58 via the passageway 86.

The rotor 16 also is provided with radial through passagway 96 leading from the outer circumferential surface 16''' to the axial passage 18 thereof and receives pin 98 therethrough for engaging the spindle 20 to enable the rotation of said rotor 16. The axial centers of the axially parallel portions of said angular passageways 78, 80, 82, 84, 86 and 88, as well as the axial center of passageway 90, intersect a circular line concentric with passage 18 and are spaced equally from their neighboring passageways and are likewise spaced equally from the outer circumference of said rotor 16. The passageways above which are employed to pass diluent to the isolated sample aliquot volumes may also be described as complementary cooperating counterpart passageways.

Figure 4:
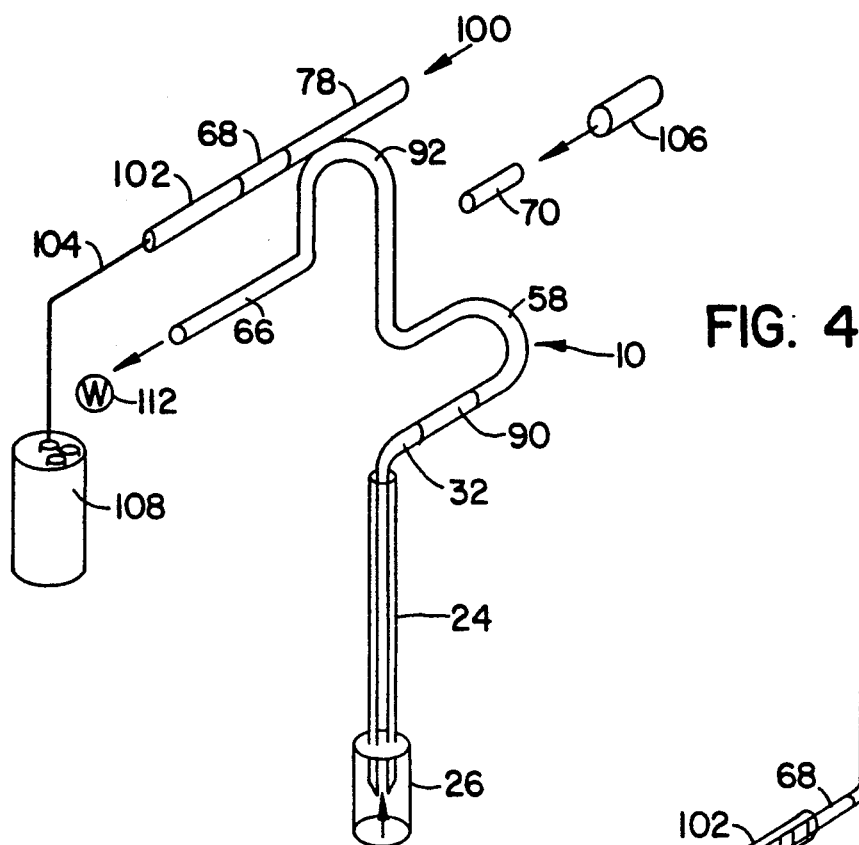
FIG. 4 is a diagrammatic representation of the valve assembly according to the invention illustrated in the loading or aspiration mode of operation.
Figure 5:
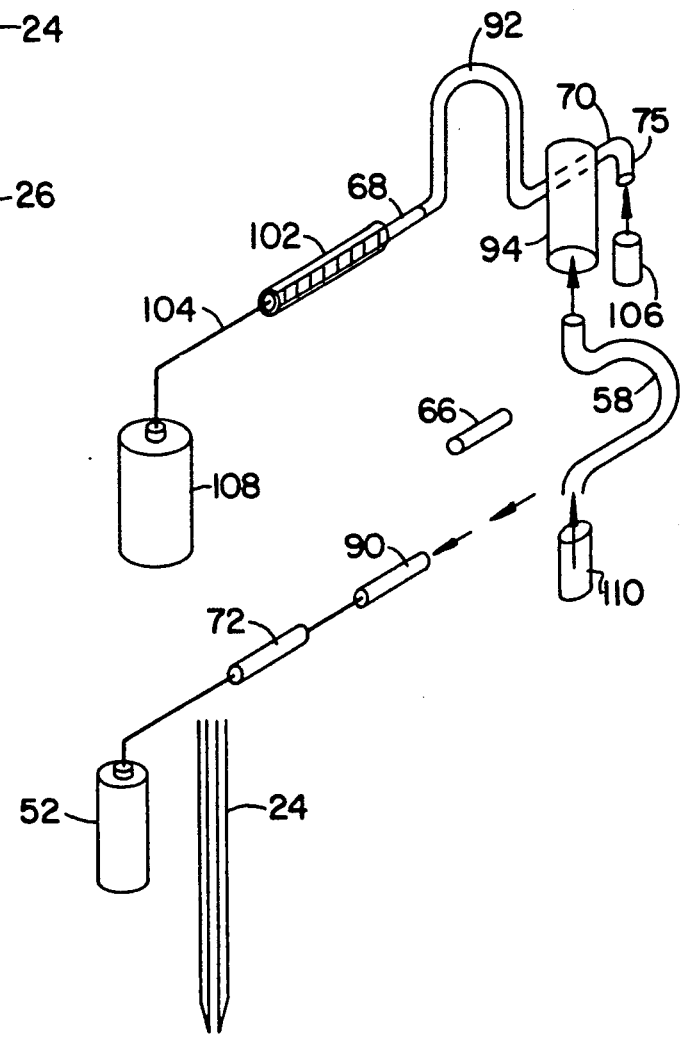
FIG. 5 is a diagrammatic representation of the valve assembly according to the invention illustrated in the segmentation or isolation mode of operation.
Figure 6:
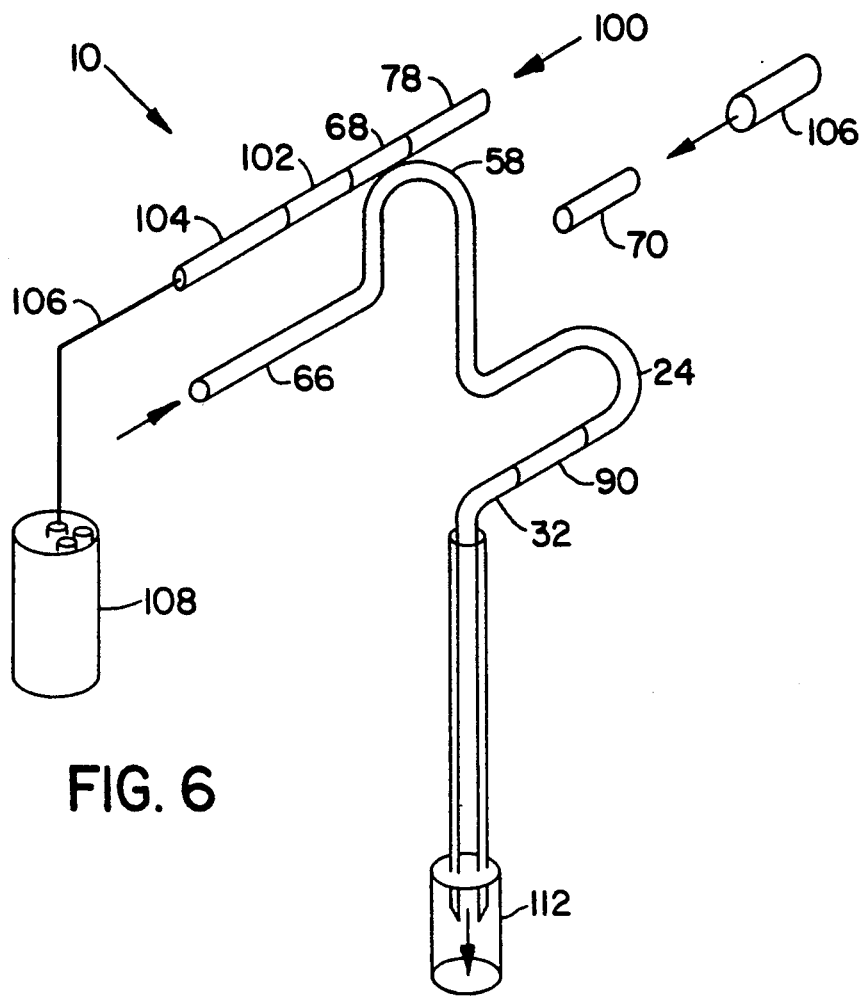
FIG. 6 is a diagrammatic representation of the valve assembly according to the invention illustrated in the completion or "backwash" mode of operation, having been returned to the condition illustrated in FIG. 4 wherein there is a partial delivery of one measured sample volume and the backwash or rinsing of the portions of the valve assembly traversed by the whole blood sample and diluent associated therewith; and, FIGS. 7A and 7B are fragmentary diagrammatic sectional detail views of the valve assembly according to the invention illustrating the disposition of the selected one measured sample volume at the segmentation mode illustrated in FIG. 5 and at the completion or backwash mode illustrated in FIG. 6, respectively.

The operation of the valve assembly 10 according to the invention may better be understood by reference to FIGS. 4 through 7B. In FIG. 4, a diagrammatic representation of the valve assembly 10 disposed in the aspiration or loading mode of operation is illustrated. While the loading element 12 can be rotated between a position selecting the automatic mode of operation via piercing needle means 22, the illustrated mode of loading operation selected is the manual mode where the whole blood sample is introduced to the valve assembly 10 from the single source 26 via the aspirator probe 24 by drawing a vacuum on the sample outlet port 66. In the aspiraton or loading mode of operation, the RBC isolating or measuring chamber (passagway 90 in the rotor 16), the first hollow loop 58 (for the WBC aliquot volume) and the seocnd hollow loop 92 (for the selected aliquot volume [which is to be lysed without dilution for use in the determination of the 5-part differential characteristic]) are aligned to define a continuous series flow path for the whole blood sample. The RBC aliquot measuring chamber 90 thus is carried by the rotor 16 while the WBC aliquot measuring chamber, hollow loop 58, is carried by the stator 14.

With the valve assembly 10 disposed in the loading mode of operation, the source of lysing reagent (lyse pump 100), the lysing reagent inlet 78 (in the rotor 16), the dedicated passageway 68 (in the stator 14), a storing conduit 102 and the coupling conduit 104 are series coupled, leading to the additional mixing and testing chamber 108 for performance of the 5-part differential determination, and are filled with lysing reagent from the previous last operation of the valve assembly. The second loop 92 is filled with fluid, such as air from air pump 106 or other inert gaseous fluid which was employed to flush the loop 92 of the prior loaded selected whole blood aliquot. The air pump 106 is blocked from delivering fluid to the loop 92 by the facing surface 14" of the stator 14.

Now the rotor 16 is ready to be rotated to place the valve assembly 10 in its segmentation or isolation (delivery) mode during which the whole blood sample aliquot volumes are isolated within the aforementioned measuring chambers. Immediately prior to the rotation of the rotor 16 to the segmentation mode, the air pump 106 is activated momentarily to direct a pulse of air to the air inlet passageway 70 to assur that no whole blood sample enters said passageway during rotation of said rotor 16.

Figure 7A:
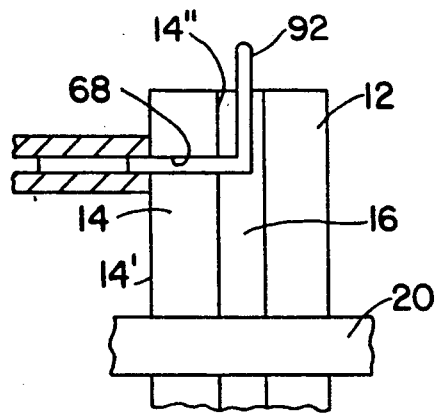
Figure 7B:
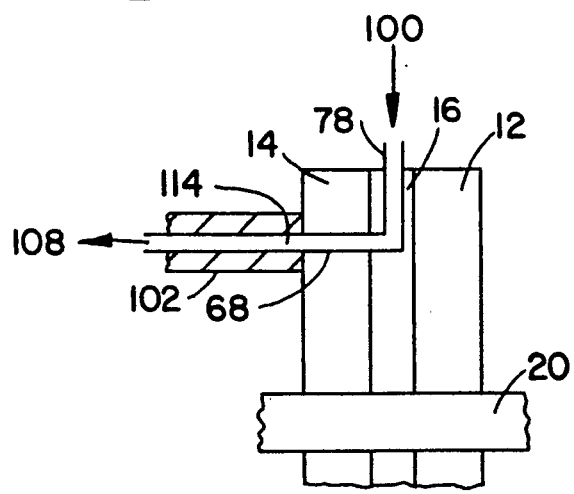

Rotation of rotor 16 is effected and the respective whole blood sample aliquots are isolated by the segmentation of the continuous body of whole blood sample in the continuous flow path defined by the serially communicating measuring chambers and sample inlet. Predetermined volumes of diluent are introduced into the valve assembly 10 via passageways 38, 54, 56 and 84 to drive the respective RBC and WBC aliquot volumes with diluent as dilutions to the respective mixing and testing chambers 52 and 108. Simultaneously, the air pump is activated to introduce air to air inlet 70, driving the selected whole blood aliquot from the hollow loop 92 to a location displaced from the rotor 16 (free of the rotor 16) and located in the storing conduit 102. air entering into the dedicated passageway 68 forcing the selected sample aliquot into the conduit 102, at least an air bubble 114 occupying the trailing end of the said selected sample aliquot volume. The position of the selected sample aliquot when same is forced from the loop 92 is represented in FIG. 7A.

With the selected sample aliquot volume displaced from the rotor 16 and the RBC and WBC aliquot volumes directed to the respective mixing and testing chambers 52 and 94 as dilutions with the predetermined volumes of diluent, the completion of this operational mode is at hand and the rotor 16 is rotated to assume its condition during the loading mode. This can be accomplished by reverse rotation of the rotor 16.

When the rotor 16 is rotated to return the valve assembly 10 to its condition during loading (FIG. 4), the lyse pump 100 is activated to introduce lysing reagent to the lysing reagent inlet passageway 78 which is aligned with the dedicated passageway 68, driving the selected blood sample aliquot (undiluted) along with said lysing reagent to said additional mixing and testing chamber 108. The flow path as existent during the aspiration or loading condition of the valve assembly 10 is returned by the reverse rotation of rotor 16 and diluent (or rinse liquid) is directed from a source 110 thereof to the passageway 66 and through the series communicating second loop 92, the first loop 58, the passageways 90 and 32 to and through the aspiration probe 24 to a waste reservoir represented by refrence character 112, completing the backwash.

Thus the lysing reagent is utilized and passed through the same valve assembly which meters and delivers sample aliquot dilutions without any contamination of the flow path traversed by the whole blood sample and the diluent associated therewith. It is believed that the invention provides the first occasion permitting the same valve assembly to be utilized to provide blood sample dilutions and lysed blood sample (undiluted) for apparatus employed to study and determine the characteristics of such samples. It should be noted that other reagents can be substituted for lysing reagent if the blood aliquots, their flow path and associated flow paths for liquids associated therewith are not to be exposed to said other reagents.

It is believed apparent that considerable variations and substitutions of equivalents are capable of being made without in any way departing from the spirit and scope of the invention as defined in the appended claims. The invention is not intended to be limited to the provision of one measured sample volume for combination with lysing reagent introduced via the valve assembly nor is it believed to be limited to merely the achievement of one, two or more dilutions for delivery to respective testing chambers.

What we claim is:

1. In a method of sampling, isolating and delivering precise volume aliquot portions of selected liquids within a single sampling and transfer valve assembly having through fluid flow paths defined therein, including the steps of defining at least one sample flow path through the valve assembly, introducing liquid sample from a source thereof to said at least one sample flow path, isolating at least one precise volume aliquot sample portion by segmenting said at least one sample flow path, the improvement comprising the additional steps of:

defining first and second dedicated passages within the valve assembly at locations displaced one from the other and from the isolated aliquot sample portion, introducing a first fluid from a source thereof to the isolated aliquot sample portion to force the isolated aliquot to the first dedicated passage at the displaced location thereof, placing the first and second dedicated passages in communicating relationship with each other, and introducing a second fluid from a source thereof to the second dedicated passage to force the isolated aliquot from the first dedicated passage with the second fluid to a predetermined location exterior of the valve assembly without contaminating any flow path within the valve assembly which has been traversed by the liquid sample or fluid other than said second fluid.

2. The method according to claim 1 in which said first fluid is inert.

3. The method according to claim 1 in which said first fluid is an inert gas.

4. The method according to claim 1 in which said second fluid is a liquid reactive with said sample.

5. The method according to claim 1 in which said second fluid is a liquid reagent.

6. The method according to claim 1 in which said first fluid is an inert gas and said second fluid is a liquid reagent.

7. The method according to claim 1 in which said first fluid is an inert gas and said second fluid is a lysing reagent reactive with said sample.

8. The method for sampling, isolating and delivering a precise volume aliquot portion of selected liquids within a single sampling and transfer valve assembly within which an internal measuring chamber is defined for holding a metered volume of a liquid sample for delivery from the valve assembly to an exterior location, said method comprising the steps of defining first and second dedicated passages within the valve assembly at locations displaced from the metering chamber, placing the first dedicated passageway in communication only with the measuring chamber, introducing a first fluid to the measuring chamber to force the metered liquid sample therein to said first dedicated passage at the displaced location thereof, placing the first and second dedicated passages in communicating relationship with each other, introducing a second fluid to the second dedicated passage to force the metered liquid sample within the first dedicated passage from said first dedicated passage with the second fluid to the location exterior of the valve assembly without the second fluid contaminating any flow path which has been traversed by the liquid sample or a fluid other than the second fluid.

9. The method according to claim 8 in which the first fluid is an inert gaseous fluid.

10. The method according to claim 8 in which the sample is whole blood, the first fluid is an inert gaseous fluid and the second fluid is a reagent reactive with whole blood.

11. The method according to claim 10 in which the second fluid is a lytic reagent.

12. A method of transferring an isolated volume of liquid sample from one isolated location within a sampling, metering and transfer valve assembly to a location exterior of the valve assembly along with a liquid reagent, comprising the steps of: defining a first dedicated isolated location within the valve assembly and a second dedicated isolated location within the valve assembly, placing said one isolated location in communication with said first dedicated isolated location, introducing a gaseous fluid only to said one isolated location forcing said volume of sample liquid only to said first dedicated isolated location, establishing communication only between said first and second dedicated isolated locations and introducing a liquid reagent to said first dedicated isolated location via said second dedicated isolated location and subsequent to receipt of the isolated volume of liquid sample in said first dedicated isolated location so as to force said isolated volume of liquid sample from the valve assembly together with said liquid reagent to a location exterior of the valve assembly without contaminating with said liquid reagent any flow paths within the valve assembly which have been traversed by said liquid sample or liquid other than said liquid reagent.

* * * * *